United States Patent [19]

Levesque

[11] Patent Number: 4,507,122

[45] Date of Patent: Mar. 26, 1985

[54] LOW DENSITY PEAT MOSS BOARD

[75] Inventor: Yvon Levesque, Montreal, Canada

[73] Assignee: Johnson & Johnson, New Brunswick, N.J.

[21] Appl. No.: 377,532

[22] Filed: May 12, 1982

Related U.S. Application Data

[63] Continuation-in-part of Ser. No. 174,403, Aug. 1, 1980, abandoned, which is a continuation-in-part of Ser. No. 7,280, Jan. 30, 1979, Pat. No. 4,215,692.

[51] Int. Cl.³ .................. A61F 13/16; A61F 13/20
[52] U.S. Cl. ..................... 604/375; 604/904; 604/374; 162/92
[58] Field of Search ............... 604/358, 367, 369, 370, 604/374, 375, 904; 162/92, 142, 148, 227

[56] References Cited

U.S. PATENT DOCUMENTS

| 610,957 | 9/1898 | Zschörner | 162/92 |
| 945,313 | 1/1910 | Franz | 162/92 |
| 2,134,930 | 11/1938 | Reynolds | 604/904 |
| 2,952,260 | 9/1960 | Burgeni | 604/374 |
| 2,962,411 | 11/1960 | Zsacsko | 162/92 |
| 3,369,544 | 2/1968 | Crockford | 604/904 |
| 3,731,686 | 5/1973 | Chatterjee | 604/904 |
| 4,215,692 | 8/1980 | Levesque | 604/370 |
| 4,226,237 | 10/1980 | Levesque | 604/374 |
| 4,305,393 | 12/1981 | Nguyen | 604/904 |

FOREIGN PATENT DOCUMENTS 463937  3/1950  Canada .................. 162/92

Primary Examiner—Richard J. Apley
Assistant Examiner—Gregory Beaucage
Attorney, Agent, or Firm—Jason Lipow

[57] ABSTRACT

A body fluid absorbent board and a method for making the same is provided with the board comprising peat moss having a particle size remaining on a 100 mesh screen and mechanical wood pulp fines having a Canadian Standard Freeness of from 60 to 500. The board has a dry density of from 0.03 to about 0.09 gm/cc and has surprising absorbent and structural integrity.

21 Claims, No Drawings

LOW DENSITY PEAT MOSS BOARD

This application is a continuation-in-part of Ser. No. 174,403 filed on Aug. 1, 1980 and now abandoned, which is a continuation-in-part of of Ser. No. 7,280 filed on Jan. 30, 1979 and now issued as U.S. Pat. No. 4,215,692 on Aug. 5, 1980.

BACKGROUND OF THE INVENTION

This invention relates to the use of peat moss in absorbent products such as diapers, sanitary napkins, tampons, and the like. More particularly, this invention relates to the use of peat moss in a form which is readily handled during use and processing and still maintains its ability to absorb body fluids.

In my co-pending application, the use of peat moss as a substitute for wood pulp fluff was disclosed and, as described therein, I have discovered that by providing a fluff of relatively coarse particulate peat moss in combination with fine mechanical wood pulp, the resulting loosely associated mixture has sufficient integreity to allow for processing into a unitary absorbent body. To allow for the undesirable native dark color of the peat moss, the aforementioned patent application discloses the use of peat moss that has been bleached. This bleaching has several drawbacks in that, irrespective of the process used, the absorbent properties of the peat is degraded to some degree. Additionally, the bleaching adds significantly to the cost of the finished product.

In dealing with the color problem of peat moss, an alternative method to bleaching is to mask the presence of the peat moss by using it in a product as a central core surrounded by more desirably colored materials. Unfortunately, the fluffed material described in the earlier application does not have sufficient integrity to be handled during the additional processing required in providing a central core and instead tends to dust, tear or otherwise degrade.

SUMMARY OF THE INVENTION

It has been discovered that peat moss may be provided as a material for absorbing body fluids in a form which will allow it to be used as a central core and, hence, obviate the need for the expensive and undesirable bleaching step. Specifically, it has been discovered that peat moss may be provided as an absorbent in the form of a low density board which, unlike the loosely associated fluff material described in my earlier application, does not derive its structural integrity from the entanglement of fibers. Instead, the bulk of its associating strength is derived from the formation of hydrogen bonds between the particulate matter when such matter has been dispersed in an aqueous slurry and then dried.

Heretofore, I have found that board-like products made with peat moss per se have not been useful in absorbent products. These boards suffered from being dense and lacking sufficient interstitial voids to act as an absorbent. It has now been observed that these drawbacks in peat moss board are overcome and a highly absorbent peat moss board can be provided if a careful selection of the starting peat moss is made to separate the peat moss into a fraction remaining on a 100 mesh screen and peat fines. To insure that a large percentage of peat fines have been separated, preferably the screening is made to utilize the fraction remaining on a 75 mesh screen, and still more preferably on about a 50 mesh screen; e.g., a 48 mesh screen. In accordance with the teachings herein, the peat moss fines are discarded and the remaining peat moss fraction is combined with mechanical wood pulp fines having a Canadian Standard Freeness of from about 60.0 to about 500.0 and preferably 150–300. An aqueous slurry is formed from this mixture and flowed onto a Fourdrinier wire where the slurry is dewatered and then dried to form the low density peat board of this invention.

The resulting peat moss board is highly absorbent and may be used in such body absorbing products as sanitary napkins, diapers, or tampons. By using the peat moss board as a central core between layers of less darkly colored material, the undesirable dark color of the peat moss is marked. In a specific embodiment, a laminate is made wherein the peat moss is sandwiched between two layers of Kraft pulp which effectively mask the dark color of the peat. It has also been discovered that the board may be used directly in an absorbent product if the brittleness and stiffness is overcome by dry compression. Such dry compression can amount to no more than embossing; i.e., embossing a pattern of indentations through one or both major surfaces of the board. Alternatively, the board can be dry compressed to greatly increase the density. Surprisingly, it has been discovered that the dry compression of this board does not effect its absorption properties. Instead, upon wetting, the board immediately recovers essentially its original thickness prior to compression. This unusual property of the peat moss board allows for dry compression so that the product is flexible and comfortable for the user prior to being wetted and, of course, is fully effective as an absorbent after being wetted.

DETAILED DESCRIPTION OF THE INVENTION

The starting peat moss is preferably of the sphagnum type and is capable of absorbing at least about 15 and preferably about 20 times its weight in water. Such peat moss is first screened to remove material such as roots and branches which are discarded. The remaining material is then separated into a usable fraction and peat fines. The usable fraction is generally that portion remaining on a 100 mesh screen. Preferably, to insure discarding a large proportion of the peat fines, the portion remaining on a 75 mesh screen and more preferably that remaining on about a 50 mesh screen is retained. For example, an excellent material can be utilized which is retained on a 48 mesh screen.

The screened peat moss fraction is, in accordance with this invention, combined with finely ground mechanical wood pulp and specifically, finely ground wood pulp selected from the group consisting of groundwood pulp, thermomechanical pulp and refiner wood pulp. Groundwood pulp is essentially trees and branches which have been debarked, cleaned and then ground into particulate matter. Refiner woodpulp differs from groundwood pulp only in that the grinding step utilizes a refiner, i.e., a disk-like device well known in the art and generally having metallic ribs at the peripheral sections thereof which last contact the wood particles and help separate the wood fibers without excessively damaging them. Thermomechanical wood pulp is similar to refiner pulp with the exception that the wood particles are heated when in the refiners, usually with steam, and this heating further aids in separating the wood fibers. The common characteristic of these mechanical pulps is that no attempt has been made to separate the fibers by chemical means although they may later, after being reduced to fine particulate matter, be subjected to chemical treatment; e.g., bleaching.

The mechanical pulps are commonly characterized by the term "Freeness" which is measured by the Canadian Standard Freeness Test (TAPPI Test Method T-227). This test essentially measures the rate of drainage of pulp and, in effect, the degree of compactness. The preferred Canadian Standard Freeness value for the mechanical wood pulp incorporated into the peat board of this invention should vary between about 60–500 and preferably from about 150—300. Mechanical pulps in quantities of as little as 5% by weight of the finished board may be employed. Preferably, about 10 to about 20% is suitable.

In addition to the screened peat moss and the mechanical wood pulp, other materials may be added to the mixture. For example, it may be desirable to add long fibered wood pulp in quantities of from 5 to about 20% by weight of the mixture to enhance handling of the mix. Such long fibered pulp can be chosen from chemically treated wood pulp such as sulphite and sulphate wood pulp.

The mixture of screened peat moss, mechanical wood pulp, and long fibered wood pulp are slurried together to form an aqueous slurry having from 0.1 to 1.0% solids with the range of choice being about 0.5%. Other ingredients may be added to the slurry, such as coloring agents, wetting agents, adhesives, or the like. The slurry is then passed onto a Fourdrinier wire and dewatered under the influence of vacuum to about 500% by weight of water. The dewatered mass is then dried into a low density board by using forced air drying at about 350° F. The density of the board may be controlled by varying such factors as the pressure difference mentioned during the dewatering step and the speed of the Fourdrinier wire. Generally, decreased vacuum and increased speed will result in a less dense product. While the conditions under which low density peat moss may be made can vary greatly, generally for a board lay down of from 15 to 35 grams of solid per square foot of board and for a vacuum pressure of from 10 to 15 inches of mercury, the speed of the Fourdrinier wire and the width of vacuum slot under which the board is exposed to the pressure differential of the vacuum should be varied so as to create a residence time of the board over the vacuum slots of about 1 to about 5 seconds. For example, with 2 slots, each having a ⅜ inch width, a Fourdrinier wire speed of about 2.5 feet per minute results in a residence time of about 1.5 seconds which, with a lay down of 20 grams per square foot, produces a low density board. Similarily, with 4 slots, each with a ⅜ inch in width, a Fourdrinier speed of 1.7 feet per minute results in a residence time of 4.4 seconds and also produces a low density peat moss board. In each of the above examples, a vacuum of about 12 inches of mercury is maintained.

Irrespective of the choice of parameters the resulting board of this invention is of low density, generally from about 0.03 to about 0.09 gm/cc. The presence of the mechanical wood pulp appears to advantageously enhance the porosity of the board which, in contrast to boards made without such mechanical wood pulp, has greater wettability and greater capillary suction capacity and has less tendancy to dust, tear or otherwise behave adversely during processing.

In a specific embodiment of this invention, a laminate is made from the board and a layer of Kraft wood pulp. The term Kraft wood pulp is well understood by the art to be used in the pulp industry for all grades of wood pulp cooked by the process in which the make up chemicals utilized is essentially sodium sulfate. It is also meant to include certain speciality grade wood pulps such as easy bleaching sulfates made from both soft woods and hard woods. This definition of the term Kraft wood pulp is exemplified by that given in the "dictionary of paper" published under the auspices and direction of the American Paper and Pulp Association, New York, N.Y., second edition 1951 at Pages 14–15. Preferably, the Kraftwood pulp is first laid down on a Fourdrinier wire from a slurry which can be about 0.1% solids. The Kraft slurry is dewatered and then passes to a second station where the peat moss and mechanical wood pulp mixture of this invention, in a slurry in the proportions described above, may be laid directly on top of the Kraft layer. This composite layer may be dewatered to produce a laminate of the low density peat moss board described herein having a layer of Kraft pulp adhered to its surface. It is preferred that the Kraft employed be bleached and have a Canadian Standard Freeness of relatively high value; e.g., about 500–600. While the proportions of the Kraft layer to the peat moss board are not critical, a suitable product results when a layer of about 0.5 to 5.0 grams of Kraft pulp per foot square is employed. The resulting product is a highly absorbent laminate with the native color of the peat moss being totally masked. In addition, the strength characteristics of the laminate are greater than that which would result from the peat board if used alone.

In still another embodiment, the board may be made even more flexible and thinner by dry compressing to the more normal densities for board of about 0.2 to about 0.8 gm/cc. It is stressed that such compression can occur only after the low density board is first formed in accordance with the teachings herein. When this requisite is complied with, the dry-compressed board exhibits certain unique properties. For example, the board is capable of taking a compression set; i.e., will maintain itself in the compressed state for an almost indefinite time as long as it remains dry. On the other hand, almost immediately upon wetting with an aqueous solution, the board will return to the low density, uncompressed state and thereby assume the absorption properties of the uncompressed board. As a result of these unique properties, absorbent products made from this board require less shelf space in storage and can be comfortably worn by a user prior to becoming wet. At the same time after being wetted, such products exhibit great absorption capacity and, of course, in the wet state, are highly flexible and comfortable. Thus, comfort is assured whenever the product is worn.

In still another embodiment, the board may be slit to increase flexibility.

To illustrate the advantages of the invention, the following examples are given:

EXAMPLE I

Raw sphagnum peat moss is classified, using a Sweco classifier, into a peat fraction having a particle size falling between 10 and 48 mesh and a peat fines fraction having a particle size of between 48 and 200 mesh. A first series of samples is prepared using a mixture of the peat fraction and, substituting for the peat fines, bleached groundwood pulp having a Canadian Standard Freeness of 200, in accordance with the teachings of this invention. For comparative purposes, a second series of samples are prepared wherein no substitution for the peat fines is made and instead a controlled amount of the peat fines are incorporated back into the mixture. Additionally, both mixtures include long fiber Kraft wood pulp having a Canadian Standard Freeness of 750. The composition of the two series of samples are as follows:

| SAMPLE Component | PERCENT BY WEIGHT A | B |
| --- | --- | --- |
| Peat (10–48 mesh) | 70 | 70 |
| Kraft (750 CSF) | 10 | 10 |
| Peat Fines (48–200 mesh) | 20 | — |
| Groundwood (200 CSF) | — | 20 |

Boards are made from each of these solids mixtures by dispersing the mixtures in water to yield a slurry having a consistency of 1.2% by weight solids. One liter of the slurry is placed in a handsheet mold measuring 12 inches by 12 inches of the type manufactured by the Williams Apparatus Company of Watertown, N.Y. The slurry is diluted to a consistency of 0.15% by weight solids in accordance with the procedure set out in TAPPI Standard Method T-2050S71. After mixing thoroughly, the water is allowed to gravity drain, leaving a wet board of about 10.0% solids. The wet moss is then dried to form a board having a density of about 0.05 gm/cc. In each case, the board contains 0.5% by weight of dry material of a wetting agent. The agent employed is a sodium dioctyl sulfo-succinate containing wetting agents manufactured by the Rohm & Haas Company and sold by them under the tradename Triton GR-5.

EXAMPLE II

Each of the series of sample boards are tested for wettability using the Droplet Sink Test. The test consists of placing a board sample measuring 5 cm by 5 cm onto a surface and then allow a single drop of 1% aqueous sodium chloride solution to fall from a height of 1.0 cm onto the surface of the board sample. The time for the drop to be absorbed into the body of the board and disappear is measured with a stop watch and reported as the Droplet Sink Time. The results are as follows:

| SAMPLE | DROPLET SINK TIME |
| --- | --- |
| A (peat fines) | 10 sec. |
| B (groundwood fines) | 1 sec. |

As is clearly evident from the above, the wettability of the board made in accordance with the teachings of this invention is substantially greater.

EXAMPLE III

Each of the series of sample boards are tested for capillary suction capacity using the Liquid Uptake Test Method. In accordance with this method, a 7.7 cm diameter board sample is placed on top of a fritted glass filter porous plate and pressed with a confining pressure of 2.5 gm/cm². The underside of the fritted glass plate is in contact with a 1% aqueous sodium chloride solution in the form of a column of such solution extending 40 cm below the porous plate. The column of solution is contained in a calibrated burette and the volume absorbed by the board sample is measured after equilibrium is attained. The same measurement is made with the column being moved to within 7½ cm below the porous plate and again, with the column moved to within 1 cm below the porous plate. The results are reported below:

| SAMPLE PRESSURE: | A (with peat fines) Solution Absorbed (cc/gm) | B (with groundwood) Solution Absorbed (cc/gm) |
| --- | --- | --- |
| −40 cm | 3.00 | 3.40 |
| −7.5 cm | 7.50 | 8.60 |
| −1 cm | 15.90 | 17.20 |

As can be seen from the above, at each pressure level, the sample board of this invention exhibited a greater capillary suction capacity.

EXAMPLE IV

Each of the series of sample boards are tested for bending strength. Strips of board measuring 8 cm × 2.5 × 1.15 cm are subjected to a bending moment of 1.5 cm with the force at fracture being measured. The results are as follows:

| SAMPLE | A (with peat moss) | B (with groundwood) |
| --- | --- | --- |
| Force at Fracture | 100 gms | 140 gms |

As can be seen from the above, the board of the invention is far stronger.

I claim:

1. A method for forming a body fluid absorbent board having structural integrity and low density comprising:
   separating peat moss into a fraction of a size at least sufficient to remain on a screen of about 100 mesh and peat fines and discarding the peat fines;
   forming a slurry of said peat moss fraction in combination with mechanical woodpulp fines having a Canadian Standard Freeness of from 60 to 500; and
   forming a board from said slurry, the board having a dry density of from about 0.03 to about 0.09 gm/cc.

2. The method of claim 1 wherein the peat moss is separated into a fraction of a size at least sufficient to remain on a screen of about 75 mesh.

3. The method of claim 1 wherein said peat moss is separated into a fraction of a size at least sufficient to remain on a screen of about 50 mesh.

4. The method of claim 1 wherein the slurry has a solids content of from about 0.1 percent to about 1.0.

5. The method of claim 1 wherein said board is formed by laying said slurry down on a Fourdrinier wire in a weight of about 15 to about 35 grams per square foot.

6. The method of claim 5 wherein the slurry is dewatered by applying a vacuum across the Fourdrinier wire, said vacuum having a pressure differential of about 10 to 15 inches of mercury.

7. The method of claim 5 wherein said vacuum is applied to have a residence time of from about 1 to about 5 seconds.

8. The method of claim 1 wherein said low density board is rendered flexible by dry compressing.

9. The method of claim 8 wherein said dry compression comprises embossing.

10. The method of claim 8 wherein said dry compressing comprises increasing the density of the board to about 0.2 to about 0.8 gm/cc.

11. The method of claim 1 wherein the board is rendered flexible by slitting.

12. A body fluid absorbent board comprising:
a mixture of peat moss having a particle size at least sufficient to remain on a screen of about 75 mesh, and mechanical wood pulp fines having a Canadian Standard Freeness of from 60 to 500; the board having a dry density of from about 0.03 to about 0.09 gm/cc.

13. The board of claim 12 wherein the peat moss has a particle size at least sufficient to remain on a screen of about 75 mesh.

14. The board of claim 13 wherein said peat moss has a particle size at least sufficient to remain on a screen of about 50 mesh.

15. The board of claim 12 wherein said mechanical wood pulp fines has a Canadian Standard Freeness of from about 60 to about 500.

16. The board of claim 12 wherein said mechanical wood pulp is present in the quantity of at least 5% by weight of the finished board.

17. The board of claim 16 wherein said mechanical wood pulp is present in quantities of about 10 to about 20% by weight of the finished product.

18. The board of claim 12 being dry compressed by embossing.

19. The board of claim 12 wherein the board is dry compressed to a density of from about 0.2 to about 0.8 gm/cc.

20. The board of claim 12 having laminated to at least one surface, a layer of Kraft pulp.

21. The board of claim 20 wherein about 0.5 to 5.0 grams of Kraft pulp per foot square is employed.

* * * * *

UNITED STATES PATENT OFFICE
CERTIFICATE OF CORRECTION

Patent No. 4,507,122　　　　　　　　　　Dated March 26, 1985

Inventor(s) Yvon Levesque

It is certified that error appears in the above-identified patent and that said Letters Patent are hereby corrected as shown below:

Column 6, line 52, claim 4 "about 1.0." should read -- about 1.0 percent --.

Signed and Sealed this

Twelfth Day of November 1985

[SEAL]

Attest:

Attesting Officer

DONALD J. QUIGG

Commissioner of Patents and Trademarks